United States Patent
Fournier

(10) Patent No.: US 10,195,256 B2
(45) Date of Patent: Feb. 5, 2019

(54) ENZYME FORMULATION FOR REDUCING SALICYLATE AND OTHER INTOLERANCE

(71) Applicant: Thea Fournier, North Andover, MA (US)

(72) Inventor: Thea Fournier, North Andover, MA (US)

( * ) Notice: Subject to any disclaimer, the term of this patent is extended or adjusted under 35 U.S.C. 154(b) by 0 days.

(21) Appl. No.: 15/698,820

(22) Filed: Sep. 8, 2017

(65) Prior Publication Data

US 2017/0368152 A1    Dec. 28, 2017

Related U.S. Application Data

(63) Continuation-in-part of application No. 14/967,746, filed on Dec. 14, 2015, now Pat. No. 9,775,887.

(51) Int. Cl.
| | |
|---|---|
| *A61K 38/43* | (2006.01) |
| *A61K 38/48* | (2006.01) |
| *A61K 38/47* | (2006.01) |
| *A61K 38/46* | (2006.01) |
| *A61K 38/54* | (2006.01) |
| *C12N 9/00* | (2006.01) |
| *C12N 9/16* | (2006.01) |
| *C12N 9/24* | (2006.01) |
| *C12N 9/76* | (2006.01) |

(52) U.S. Cl.
CPC ........ *A61K 38/4826* (2013.01); *A61K 38/465* (2013.01); *A61K 38/47* (2013.01); *A61K 38/54* (2013.01); *C12N 9/00* (2013.01); *C12N 9/16* (2013.01); *C12N 9/2402* (2013.01); *C12N 9/6427* (2013.01); *C12Y 301/03* (2013.01); *C12Y 302/01* (2013.01); *C12Y 302/01026* (2013.01); *C12Y 302/01108* (2013.01); *C12Y 304/21001* (2013.01)

(58) Field of Classification Search
None
See application file for complete search history.

(56) References Cited

U.S. PATENT DOCUMENTS

| | | | |
|---|---|---|---|
| 9,775,887 B2 * | 10/2017 | Fournier | ............... A61K 38/465 |
| 2006/0115467 A1 | 6/2006 | Pangborn et al. | |
| 2007/0116695 A1 | 5/2007 | Fallon | |
| 2008/0112944 A1 * | 5/2008 | Pangborn | ............... C12N 9/107 424/94.2 |
| 2010/0260857 A1 | 10/2010 | Fallon | |
| 2017/0000830 A1 | 1/2017 | Saini | |

OTHER PUBLICATIONS

Vital-Zymes Complete. Prothera, Inc. p. 1, In2; p. 2, Supplement Facts, In10-11, 17-18; p. 6, In10; 2007.
PCT Written Opinion.
Prothera Publication: "Vital-Zymes Complete".
Written Opinion of ISR in PCT/US2016/065813.

* cited by examiner

*Primary Examiner* — Ralph J Gitomer
(74) *Attorney, Agent, or Firm* — Eric P. Mirabel, JD, LLM

(57) ABSTRACT

Disclosed is a formulation of the following enzymes: Beta Glucanase, Chymotrypsin, Phytase, Lactase, and Invertase, which has been found to be effective in treating salicylate intolerant people, and causing a significant improvement in a wide variety of pathologies and symptoms, including, but not limited to: acid reflux disease, stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy. The formulation is also for treating or reducing intolerance of gluten, corn or soy.

9 Claims, No Drawings

ENZYME FORMULATION FOR REDUCING SALICYLATE AND OTHER INTOLERANCE

BACKGROUND

Many people suffer from food intolerance. It is believed that many such people's intolerances can be traced to use of pesticides, and/or genetically engineered foods, which adversely affect liver pathways, inhibit enzymes, and disrupt amino acids in the body which ultimately can lead to food intolerances.

Intolerance to gluten has been widely discussed. Less well known, but equally widespread, is intolerance to salicylates and histamines. Salicylates are compounds that are manufactured synthetically and found in artificial colorings and flavorings, solvents, many personal care products and elsewhere in some foods as additives/preservatives. These salicylate compounds are also naturally occurring in many plant foods, including fruits, vegetables, and herbs/spices. In the course of many years of consulting and observing thousands of clients, the inventor has found that patients who follow the recommended dietary restrictions (which reduce or substantially eliminate salicylates), experience a significant improvement in a wide range of symptoms and pathologies. Eliminating salicylates and adhering to the recommendations, appears to be highly effective in treating a wide range of symptoms/conditions, including, but not limited to: acid reflux disease, stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy.

SUMMARY

A formulation of the following enzymes: Beta Glucanase, Chymotrypsin, Phytase, Lactase, and Invertase, has been found to be effective in treating salicylate intolerant people, and causing a significant improvement in a wide variety of symptoms/conditions, including, but not limited to: acid reflux disease, stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy. It may also be used to treat intolerance of gluten, corn or soy. It is believed that the formulation catalyzes breakdown of salicylate compounds in vivo by restoring the function of an impaired Sulfation Detoxification Pathway in the liver and helping to increase low sulfate levels in subjects. It has been reported that without normal levels of sulfates in the body, the Phenol-Sulfotransferase (PST) enzymes in the liver cannot metabolize salicylates.

More particularly, the preferred dosages of the enzymes in the formulation are as follows: Beta Glucanase: 200 BGU; Chymotrypsin (from porcine, preferably, or beef) 3.0 mg (or not less than 3000 USP units); Phytase 30 FTU; Lactase 600 ALU, and Invertase 600 INVU. More preferred, is ingesting two or more of the formulation with the foregoing contents with each meal. A preferred carrier for the formulation is a vegetable capsule (including, mostly cellulose and distilled water). Most preferred is that the formulation be free of any of the following: casein, gluten, dairy, egg, soy, corn, peanuts, tree nuts, and fish.

A discussion of testing and demonstrating the safety and efficacy of the formulation is set forth below in the Detailed Description.

DETAILED DESCRIPTION

It has been found over decades of study, that people who adopt a dietary restriction plan which eliminates foods and food products containing salicylates experience significant improvement in some, but not limited to, the following symptoms and conditions: acid reflux disease, stuttering, migraines, ADHD, behavioral deficits, Tourettes disease, seizures, autism (ASD), atrial fibrillation, anxiety, depression, joint pain, cognitive and perceptual disorders, respiratory difficulties and non-diabetic neuropathy. A study was designed to test the formulation, as set forth in the Example below.

The preferred dosages of the enzymes set forth in the Summary are not the only dosages possible, and other more optimal dosages and dosing regimes may be discovered with routine experimentation, now that the preferred dosages are known. The routine experimentation would involve providing different dosages under different regimes, using behavioral kinesiology to determine the appropriate dosage and optimal regime for each individual child or adult in the case study, and determining which patients improved most in their monitored diseases and conditions.

The starting point for determining optimal dosing and an optimal regime, is the preferred dosages, administered once a day, as above. Variations could be doubling, halving, or otherwise and reducing the quantities of one or more of the enzymes in a formulation. The dosing regime modifications could include increasing or reducing the number of administrations of the formulation each day for patients in a particular group. Such experimentation is routine in the pharmaceutical industry.

Example—Clinical Study 89 study participants intolerant of salicylates were selected using muscle testing, a self-reported questionnaire with 320 symptoms indicative of the condition, together with participant's history and a participant examination. The study involved an enzyme formulation designated Theazyme-S with the active ingredients: Beta Glucanase, 200 BGU; Chymotrypsin, not less than 3000 USP units; Phytase 30 FTU; Lactase 600 ALU and Invertase 600 INVU, which was administered daily.

The 89 participants were randomized into Group I (62 participants) and Group II (27 participants). Group I participants avoided salicylates for at least 6 months and found that many of their adverse symptoms had improved or totally subsided by start of the active phase of Theazyme administration. Group II participants continued on their regular diet (all of which included salicylates) for at least 6 months. All Group II participants reported no improvement in any of their adverse symptoms at the end of the initial 6 month period and the start of the active phase.

At the end of the initial period, all Group I and Group II participants commenced daily dosing of Theazyme. All participants were muscle tested after two months and after three months. All participants' muscle tested strongly after three months (end of the active phase), meaning they were then tolerant to salicylate foods. Group I participants were permitted to consume salicylate-containing foods during the active phase of the trial and all reported doing so; and Group II participants continued on their regular salicylate-containing diets during the active phase.

Among the indications monitored (both at the close of the initial phase for all participants in Group II, and at the end of the active phase of the trial for all participants) were attention deficit hyperactivity disorder with marked hyperactivity, chronic acid reflux and migraine headaches. All three indications are associated with salicylate intolerance.

Regarding ADHD, 19 participants indicated marked hyperactivity, and at the end of the active phase, 15 participants (eight from Group 1 and seven from Group II) reported significant improvement in marked hyperactivity during the active phase, and three of the participants (two from Group I and one from Group II) reported no marked hyperactivity during the active phase. One Group I participant had no noticeable improvement.

Eighteen participants indicated chronic acid reflux, and at the end of the active phase, seven participants (five from Group 1 and two from Group II) reported marked improvement in pain and duration of the reflux episodes during the active phase, and eleven of the participants (eight from Group 1 and three from Group II) reported no reflux episodes during the active phase.

Sixteen participants indicated migraine headaches, and at the end of the active phase, six participants (four from Group I and two from Group II)) reported marked improvement in pain and duration of the migraine episodes during the active phase, and nine of the participants (six from Group 1 and three from Group II) reported no migraine episodes during the active phase. One Group I participant had no noticeable improvement.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating symptoms of one or more of the following diseases or conditions: acid reflux disease, neuropathy, behavioral deficits, anxiety, depression, joint pain, cognitive and perceptual disorders, and respiratory difficulties comprising, administering to a subject in need thereof an effective amount of a formulation consisting essentially of the enzymes: Beta Glucanase, Chymotrypsin, Phytase, Lactase and Invertase.

2. The method of claim 1 wherein the quantities of the enzymes in the formulation are: Beta Glucanase, 200 BGU; Chymotrypsin, not less than 3000 USP units; Phytase 30 FTU; Lactase 600 ALU and Invertase 600 INVU.

3. The method of claim 1 wherein the Chymotrypsin is derived from porcine.

4. The method of claim 3 wherein the quantity of Chymotrypsin is 3000 USP units.

5. The method of claim 1 wherein the Chymotrypsin is derived from beef.

6. The method of claim 5 wherein the quantity of Chymotrypsin is 3000 USP units.

7. The method of claim 1 wherein the diseases or conditions are ADHD and migraines.

8. The method of claim 1 wherein the formulation is administered at least once per day.

9. The method of claim 1 wherein the neuropathy is non-diabetic neuropathy.

\* \* \* \* \*